(12) United States Patent
Manaresi et al.

(10) Patent No.: US 8,388,823 B2
(45) Date of Patent: Mar. 5, 2013

(54) METHOD AND APPARATUS FOR THE SEPARATION AND QUANTIFICATION OF PARTICLES

(75) Inventors: Nicolò Manaresi, Bologna (IT); Gianni Medoro, Casalecchio di Reno (IT)

(73) Assignee: Silicon Biosystems S.p.A., Bologna (IT)

( * ) Notice: Subject to any disclaimer, the term of this patent is extended or adjusted under 35 U.S.C. 154(b) by 1449 days.

(21) Appl. No.: 11/724,697

(22) Filed: Mar. 16, 2007

(65) Prior Publication Data

US 2008/0041723 A1    Feb. 21, 2008
US 2012/0273356 A9    Nov. 1, 2012

Related U.S. Application Data

(63) Continuation of application No. 11/651,313, filed on Jan. 8, 2007, which is a continuation of application No. PCT/EP2005/053235, filed on Jul. 6, 2005.

(30) Foreign Application Priority Data

Jul. 7, 2004 (IT) .................................. BO04A0420

(51) Int. Cl.
*B01D 57/02* (2006.01)
(52) U.S. Cl. ........................................ 204/547; 204/643
(58) Field of Classification Search .................. 204/547, 204/643
See application file for complete search history.

(56) References Cited

U.S. PATENT DOCUMENTS

| 5,252,493 | A  | 10/1993 | Fujiwara et al. |
| 5,279,493 | A  | 1/1994  | Halder |
| 5,888,370 | A  | 3/1999  | Becker et al. |
| 5,945,281 | A  | 8/1999  | Prabhu |
| 6,149,789 | A  | 11/2000 | Benecke et al. |
| 6,203,683 | B1 | 3/2001  | Austin et al. |
| 6,264,815 | B1 | 7/2001  | Pethig et al. |
| 6,294,063 | B1 | 9/2001  | Becker et al. |
| 6,824,664 | B1 | 11/2004 | Austin et al. |

(Continued)

FOREIGN PATENT DOCUMENTS

| DE | 3931851  | 4/1992 |
| DE | 10203636 | 2/2004 |

(Continued)

OTHER PUBLICATIONS

Altomare, et al, (2002), "Levitation and Movement of Human Tumor Cells Using a Printer Circuit Board Device Based on Software-Controlled Dielectrophoresis", pp. 474-479; University of Bologna, Bologna, Italy.

(Continued)

*Primary Examiner* — J. Christopher Ball
(74) *Attorney, Agent, or Firm* — Marshall, Gerstein & Borun LLP

(57) ABSTRACT

The invention pertains to a method and apparatus to separate and quantify particles using time-variable force fields. The force fields can be for dielectrophoresis (positive or negative), electrophoresis, or electrohydrodynamic. In one aspect, the fields are translated and/or modified in space at a speed substantially comparable to the speed of translation of the fastest particles in the sample. The translation and/or modification of the force fields can also occur with varying speed. In another aspect, the field is translated and/or modified in a first direction at high speed. In another aspect, the quantity or size of the particles is determined by an indirect measurement of the speed of movement after varying the force field by means of a relationship between the speed of movement and the volume of the particles. This invention also pertains to an apparatus to produce appropriate field configurations necessary for the selective movement of particles.

7 Claims, 9 Drawing Sheets

U.S. PATENT DOCUMENTS

| | | |
|---|---|---|
| 6,830,729 B1 | 12/2004 | Holl et al. |
| 6,875,329 B2 | 4/2005 | Washizu et al. |
| 6,888,721 B1 | 5/2005 | Moghaddam et al. |
| 6,911,132 B2 | 6/2005 | Pamula et al. |
| 6,977,033 B2 | 12/2005 | Becker et al. |
| 7,307,328 B2 | 12/2007 | Meyer et al. |
| 7,488,406 B2 | 2/2009 | Hughes et al. |
| 2002/0031838 A1 | 3/2002 | Meinhart et al. |
| 2002/0036139 A1 | 3/2002 | Becker et al. |
| 2002/0070114 A1 | 6/2002 | Miles |
| 2002/0125138 A1 | 9/2002 | Medoro |
| 2002/0132316 A1 | 9/2002 | Wang et al. |
| 2003/0044832 A1 | 3/2003 | Blankenstein |
| 2003/0047456 A1 | 3/2003 | Medoro |
| 2003/0073110 A1 | 4/2003 | Aritomi et al. |
| 2004/0011652 A1 | 1/2004 | Bressler |
| 2004/0055891 A1 | 3/2004 | Pamula et al. |
| 2004/0058450 A1 | 3/2004 | Pamula et al. |
| 2004/0063196 A1 | 4/2004 | Muller et al. |
| 2004/0191789 A1 | 9/2004 | Manaresi et al. |
| 2004/0209354 A1 | 10/2004 | Mathies et al. |
| 2005/0014146 A1 | 1/2005 | Manaresi et al. |
| 2005/0214736 A1 | 9/2005 | Childers et al. |
| 2006/0051775 A1 | 3/2006 | Bianchi |
| 2006/0086309 A1 | 4/2006 | Manger et al. |
| 2006/0177815 A1 | 8/2006 | Soh et al. |
| 2006/0228749 A1 | 10/2006 | Wang et al. |
| 2007/0051412 A1 | 3/2007 | Heath et al. |
| 2008/0246489 A1 | 10/2008 | Coster et al. |
| 2008/0264068 A1 | 10/2008 | Nakasuka et al. |
| 2009/0218223 A1 | 9/2009 | Manaresi et al. |

FOREIGN PATENT DOCUMENTS

| | | | |
|---|---|---|---|
| DE | 19500660 | | 12/2007 |
| EP | 1145766 | | 8/2007 |
| EP | 1304388 | | 2/2008 |
| EP | 1179585 | | 7/2008 |
| WO | WO-91/08284 | | 6/1991 |
| WO | WO-98/04355 | | 2/1998 |
| WO | WO-99/17883 | | 4/1999 |
| WO | WO-00/28313 | | 5/2000 |
| WO | WO 00//69565 | | 11/2000 |
| WO | WO-02/12896 | | 2/2002 |
| WO | WO-03/014739 | | 4/2004 |
| WO | WO-03/045556 | | 4/2004 |
| WO | WO-2004/071668 | | 8/2004 |
| WO | WO-2005/098395 | | 10/2005 |
| WO | WO 2006003214 | * | 1/2006 |
| WO | WO-2005/060432 | | 3/2007 |
| WO | WO-2007/049103 | | 5/2007 |
| WO | WO-2007/049120 | | 10/2007 |
| WO | WO-2009/022222 | | 6/2010 |

OTHER PUBLICATIONS

Manaresi, et al, (2003), "A CMOS Chip for Individual Cell Manipulation and Detection", pp. 2297-2305, IEEE Journal of Solid State Circuits, vol. 38, No. 12 (Dec. 2003).

Medoro, et al, "A Lab-On-A-Chip for Cell Separation Based on the Moving-Cages Approach", University of Bologna, Bologna, Italy.

Medoro, et al., (2003), "A Lab-On-A-Chip for Cell Detection and Manipulation", pp. 317-325, IEEE Sensors Journal, vol. 3, No. 3, Jun. 2003.

Medoro, et al., (2004), "Dielectrophoretic Cage-Speed Separation of Bio-Particles", IEEE 0-7803-8692-2/04, pp. 76-79; University of Bologna, Bologna, Italy.

Ohara, et al, Ratcheting Electrophoresis Microchip (REM) for Programmable Transport and Separation of Macromolecules, 2001 ASME International Mechanical Engineering Congress and Exposition, Nov. 11-16, 2001, New York City, NY, pp. 619-628, MEMS—vol. 3.

Pethig, et al., "Enhancing Traveling-Wave Dielectrophoresis With Signal Superposition—A New Method for Cell Separatin and Chacarterization and for Monitoring cell Physiological Changes", IEEE Engineering in Medicine and Biology Magazine, pp. 43-50; Nov./Dec. 2003.

Rousselet, et al., (1994), "Directional Motion of Brownian Particles Induced by a Periodic Asymmetric Potential", pp. 446-448, Nature, vol. 370.

International Preliminary Report on Patentability for corresponding International application No. PCT/EP2005/053235, dated Jan. 9, 2007.

International Search Report and Written Opinion for corresponding International application No. PCT/EP2005/053235, mailing date May 2, 2006.

Cheung et al., Impedance spectroscopy flow cytometry: on-chip label-free cell differentiation, Cytometry Part A, 65A(2):124-32 (2005).

Gascoyne et al., Dielectrophoresis-based programmable fluidic processors, Lab Chip, 4:299-304 (2004).

Gascoyne et al., Particle separation by dielectrophoresis, Electrophoresis, 23(13): 1973-83 (2002).

Green et al., Ac Electrokinetics: a survey of sub-micrometre particle dynamics, J. Phys. D: Appl. Phys., 33:632-41 (Dec. 10, 1999).

Hughes, Strategies for dielectrophoretic separation in laboratory-on-a-chip systems, Electrophoresis, 23(16): 2569-82 (2002).

Jones, An electromechanical interpretation of electrowetting, J. Micromech. Microeng., 15(6):1184-7 (2005).

Nieuwenhuis et al., Near-field optical sensors for particle shape measurements, Sensors Journal IEEE, 3(5):646-51 (2003).

Petersson et al., Carrier medium exchange through ultrasonic particle switching in microfluidic channels, Anal. Chem., 77:1216-21 (2005).

International Search Report and Written Opinion for PCT/IB2006/000636, dated Sep. 8, 2006.

International Preliminary Report on Patentability for PCT/IB2006/000636, dated Apr. 29, 2008.

International Search Report and Written Opinion for PCT/IB2006/001984, dated Feb. 27, 2007.

International Preliminary Report on Patentability for PCT/IB2006/001984, dated Dec. 3, 2007.

International Search Report and Written Opinion for PCT/IB2007/000751, dated Nov. 16, 2007.

Berthier et al., NSTI Nanotech 2005, vol. 1 (2005), www.nsti.org.

Fiedler et al., Electrocasting formation and structuring of suspended microbodies using A.C. generated field cages, Microsystem Technologies, Berlin, Germany, pp. 1-7 (Dec. 1, 1995).

Fuhr et al., Positioning and manipulation of cells and microparticles using miniturized electric field traps and travelling waves, Sensors and Materials, 7(2):131-46 (1995).

Milner et al., Dielectrophoretic classification of bacteria using differential impedance measurements, Electronics Letters, 34(1):66-8 (1998).

Ohta et al., Tech. Dig. Of the Solid State Sensor, Actuator and Microsystems, Workshop, pp. 216-9 (2004).

Schnelle et al., Three-dimensional electric field traps for manipulation of cells—calculation and experimental verfication, Biochem. Biophys. Acta, 1157(2):127-40 (1993).

Suehiro, The dielectrophoretic movement and positioning of a biological cell using a threedimensional grid electrode system, J. Phys. D: Appl. Phys., 31:3298-305 (1998).

International Preliminary Report on Patentability for PCT/IB2007/000751, dated Sep. 30, 2008.

International Search Report and Written Opinion for PCT/IB2006/002965, dated Jun. 15, 2007.

International Preliminary Report on Patentability for PCT/IB2006/002965, dated Apr. 29, 2008.

Nonfinal office action, U.S. Appl. No. 12/294,860, mail date Jan. 27, 2012.

Nonfinal office action, U.S. Appl. No. 12/091,367, mail date Mar. 25, 2011.

Final office action, U.S. Appl. No. 12/091,367, mail date Nov. 1, 2011.

International Search Report and Written Opinion for PCT/IB2010/000615, mailing date Aug. 26, 2010.

International Preliminary Report on Patentability for PCT/IB2010/000615, dated Sep. 20, 2011.

* cited by examiner

METHOD AND APPARATUS FOR THE SEPARATION AND QUANTIFICATION OF PARTICLES

REFERENCE TO RELATED APPLICATIONS

This application is a continuation of U.S. patent application Ser. No. 11/651,313 filed Jan. 8, 2007, which is a continuation of International Patent Application Serial No. PCT/EP05/53235 filed Jul. 6, 2005, which claims priority to Italian Patent Application Serial No. BO2004A000420 filed Jul. 7, 2004.

FIELD OF THE INVENTION

This invention pertains to methods and apparatuses to separate particles with different physical properties, and/or to measure the quantity or size of particles. The invention mainly finds application in the analysis and separation of biological samples.

BACKGROUND OF THE INVENTION

The patent application PCT/WO 00/69565 to G. Medoro describes an apparatus and method for manipulating and locating particles using closed cages of dielectrophoretic potential. Besides this, PCT/WO 00/69565 teaches methods of separation. A first method is based on the differential action, on populations of different cells, of dielectrophoresis (DEP) negative (NDEP) and positive (PDEP), and does not permit discriminating particles if they are both subject to NDEP or PDEP. Other methods of separation instead require using information from sensors integrated in the device, and cannot be implemented when there are no such sensors.

Many other methods of separation are known that nevertheless require using flows of liquid, which is an undesirable characteristic in many applications, since it requires generating well controlled flows. A review of these methods, above all as concerns the use of dielectrophoresis is given in *Electrophoresis* 2002, 23, 2569-2582 M P. Hughes, and in *Electrophoresis* 2002 23, 1973-1983 P. R. C. Gascoyne, J Vykoukal, and in the related bibliographical references.

In particular, the patent U.S. Pat. No. 5,888,370 to Becker et al. teaches among other things to use dielectrophoresis to determine the height of particles in a speed-profile of liquid flow, to which the separation of the particles follows.

Other methods of separation based on dielectrophoresis do not require using flows of liquid, but they utilize so-called Travelling waves (TWD). These methods are based on the application to an array of electrodes of sinusoidal voltages at suitably phase-shifted radio frequencies (e.g. 0, 90, 180, 270 degrees). The result is an electric field that travels in space at a speed (VTW) equal to the distance between the electrodes with the same phase divided by the period of the single sine voltage. The phase-shift between the polarization induced on the particle and the electric field that generates it causes a translation of the particle, at a speed of orders of magnitude less than VTW, and asynchronous with it. Accordingly it is not possible to maintain an accurate control on the position of the particles after separation, which may be desirable in many applications, for instance if it is wished to determine the quantity of separated particles by placing them above sensors.

The limitations of the known art are superseded by this invention that permits separating particles even if they are subject to the same force (e.g. NDEP), it requires no flow of liquid, and it permits keeping a control on the position of the particles during and after separation or measurement.

SUMMARY OF THE INVENTION

The invention pertains to a method and apparatus to separate particles using time-variable, non-uniform force fields. The force fields can be for dielectrophoresis (positive or negative), electrophoresis or electrohydrodynamic motion, characterized by a set of stable-equilibrium points for the particles.

The physical properties of the particles determine the speed with which they move, subject to the action of the force field. A first objective is to isolate the particles that are most affected by the force field, in other words the fastest particles. A second objective is to isolate the particles that are less affected by the force field, in other words the slower particles. A third objective is to separate in one direction the ones that are most affected by the force field and in the opposite direction the ones that are less affected. An additional objective is to indirectly quantify groups of particles of one type determining the response speed of groups of them or the size of single particles.

In one aspect of the method, the stable-equilibrium points of the field are translated in space at a speed substantially comparable to the speed of translation of the fastest particles in the sample so that only these follow by changing position, while the slowest particles are not affected.

According to the invention the translation of these points of equilibrium can also occur with varying speed, which is especially useful when this happens with periodic law on a field with spatial periodicity. In one aspect of the method, the points of equilibrium of a force field with spatial periodicity are translated in a first direction at high speed, for such a period of time as to cause a movement equal to the spatial period of the field, and at low speed in a second direction, opposite to the first one, for such a period of time as to cancel the overall movement of the field, causing the translation of the slowest particles in the second direction and no movement of the fastest particles.

In an additional aspect of the method, the stable-equilibrium points of the field are translated in a first direction at high speed, for such a period of time as to cause a movement equal to the spatial period of the field minus a quantity corresponding to the period of the electrodes generating it, causing the translation of the fastest particles in the first direction and of the slowest particles in the opposite direction.

In another aspect of the method the particles, subject to the action of the force of gravity, suffer a different attenuation of the effects of the forces applied such as to induce a variation on the speed of movement, therefore determining the separation of the particles.

In another aspect of the method, the particles are grouped by the force of dielectrophoresis and their different response speed to translations of the field is utilized to indirectly determine the quantity of particles in the group or the size of the particles.

Another aspect of the invention is a device that permits advantageously producing some of the aforesaid methods, composed of just two array of electrodes to which different varying-time potentials are applied.

Hereinafter, the term particles will be used to indicate micrometric or nanometric, natural or artificial entities, such as cells, subcellular components, viruses, liposomes, niosomes, microbeads and nanobeads, or even smaller entities such as macro-molecules, proteins, DNA, RNA, etc, as well as drops of liquid immiscible in the suspension medium, for example oil in water or water in oil.

DETAILED DESCRIPTION OF THE INVENTION

The purpose of the invention is to create a method and an apparatus for the separation of particles according to their physical properties or their quantification or the determination of their size. The method is based on using a non-uniform force field (F). This field can for instance be a field of dielectrophoresis (DEP) negative (NDEP) or positive (PDEP), an electrophoretic field (EF) or a field of electrohydrodynamic motion (EHD).

Generation of the Force Field

Figure 1:
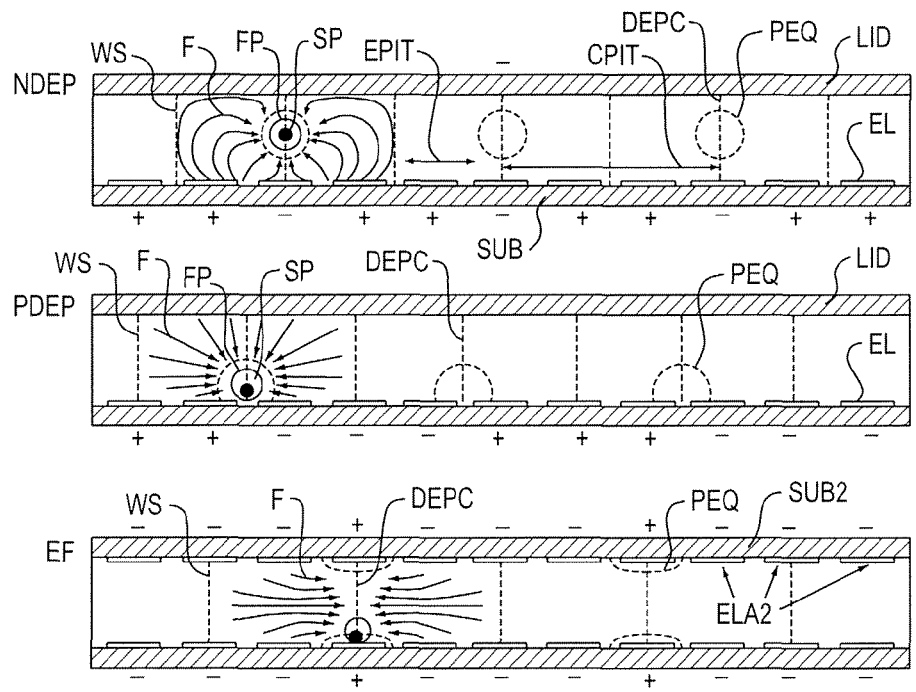
FIG. 1 shows the principle of generation of the force field by means of an array of electrodes.

FIG. 1 shows some methods of generating the force field, according to the known art, using an array of electrodes (EL), made on at least one substrate (SUB, SUB2). A cover (LID), that can in its turn be an electrode, bounds a micro-chamber, in use filled with a liquid having a certain viscosity. In the case of DEP, the applied voltages are periodic voltages (preferably sinusoidal) in phase (+) and counter-phase (−). Voltages in counter-phase are understood to be voltages phase-shifted by 180 degrees. The field generates a force (F) that acts both on faster particles (FP) and on slower particles (SP), both attracted toward points of equilibrium (PEQ). Depending on the configuration of the voltages applied it is possible to identify coordinates (DEPC) corresponding to the position of the point of stable equilibrium (PEQ), and coordinates (WS) corresponding to points of unstable equilibrium, that is to the boundary of the basin of attraction of different stable-equilibrium points. These lines ideally form a sort of watershed that determines toward which point of stable equilibrium the particle tends to go. In the case of negative DEP (NDEP), it is possible to make closed force cages if the cover (LID) is a conductive electrode. The point of equilibrium (PEQ) is normally found in the liquid at a certain height compared to the electrodes, so that the particles (SP, FP) are, in steady-state, in levitation. In the case of positive DEP (PDEP), the point of equilibrium (PEQ) is normally found in correspondence with the surface on which the electrodes are made, and the particles (FP, SP) are, in steady-state, in contact with it. For PDEP it is not necessary to have additional electrodes in the cover because the points of equilibrium of the PDEP correspond to maxima of the electric field.

The field can have a spatial periodicity (CPIT) that is a multiple of the periodicity of the electrodes (EPIT), in the cases in which this can be defined.

Property of Separation

Figure 2:
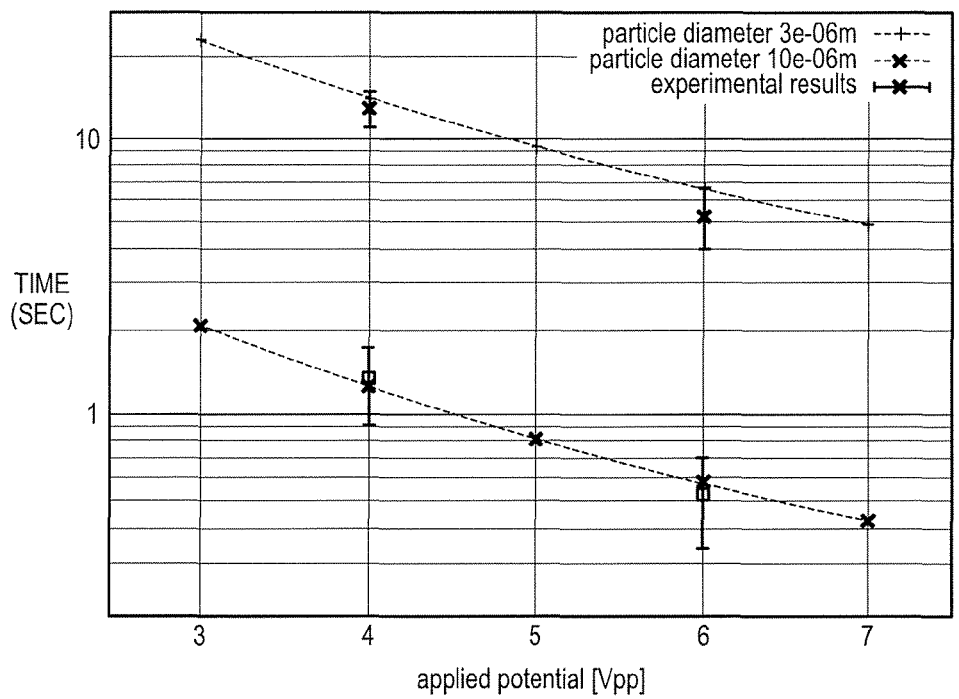
FIG. 2 shows some experimental data and simulations of speed of translation of microbeads of polystyrene.

When the points of stable equilibrium of the force field (F) are moved by a step (EPIT) changing the configuration of the voltages (+, −) applied to the electrodes (EL), the particles converge toward the new point of equilibrium with a time that substantially depends on the ratio between the force of viscous friction and the force of the field (F). FIG. 2 shows some experimental data and simulations of the necessary time to complete a movement equal to half an EPIT step following the movement of the points of equilibrium of the force field of an EPIT step (in the specific case equal to 25 μm), for microbeads of polystyrene subject to NDEP, respectively 3 μm and 10 μm in diameter, depending on the peak-to-peak amplitude of the sine voltage applied to the electrodes. For the same particle material, the force of the field (F) is proportional to the volume, that is to the cube of the radius, while the viscous force is proportional to the radius, so particles with a greater radius will move faster (FP) than those of smaller diameter (SP). This effect is exploited, in accordance with the invention, to separate the particles or quantify groups of particles or to determine the size of such particles, as described hereunder. It is evident to experts in the sector with ordinary abilities that the difference in speed can also occur for particles of the same diameter (same force of viscous friction), on which the force field (F) acts with different intensity. In this case the particles on which it acts with greater intensity (FP) are faster than those on which it acts with less intensity (SP).

It is moreover evident that the method is also effectively applied in cases in which the field acts with the same force on all the particles, but the viscous friction is different due, e.g. to the different material or shape of the particles.

The principle of the separation exploits the balancing between a force generated by the field (F), not uniform in the space and that moves in a controlled manner, and a force that acts uniformly. This can be the viscous friction, as described above, but also, for example, the force of gravity. For example, two particles on which the field (F) acts with the same force and that have the same viscous friction (for instance having the same diameter) would nevertheless be able to have different mass. In this case, tilting the device so that the force of gravity has a non-null component in the direction of movement of the force field (F) will cause the particles to have a different speed, so that it is anyhow possible to apply the method.

In general, one different physical property between the particles is enough to permit separation. The physical properties according to which the particles are discriminated can for instance be the diameter, shape, material of which they are made or the relative proportion and the arrangement of the component materials, or even the surface properties. In other cases they can include the electric charge. They can obviously also be combinations of the aforesaid properties. By way of example, but without restricting the purpose of the invention we can mention the separation of:

cells of the same type but of different dimensions;
cells of the same type but with different functional properties;
sperm cells with morphological anomalies from normal sperm cells;
cells of the same dimensions but with a different composition of the cytoplasm;
apoptotic cells from vital cells;
cells infected with viruses or intracellular parasites from non-infected cells;
cells infected with AIDS from non-infected cells;
cells infected with malaria from non-infected cells;
cells infected with Chlamydia from non-infected cells;
cells decorated with antibodies from non-decorated cells;
cells of different types:
red blood cells from lymphocytes;
red blood cells from erythromyeloid cells;
sperm cells from vaginal epithelial cells;
liposomes of different dimensions but with the same content;
microbeads of different dimensions;
polystyrene beads of 3 µm and 10 µm;
beads of 6 µm and 15 µm;
microbeads of the same dimensions but with different surface functionalities:
beads of 3 µm functionalized with ammine groups and non-functionalized beads;
microbeads of the same dimensions but with different surface charge;
positively charged microbeads from neutral microbeads;
cells from viruses
viruses of different types
fragments of DNA of different molecular weight;
proteins with a different ratio between mass and charge.

Method of Separation With Aperiodic Speed (Single Wave)

Figure 3:
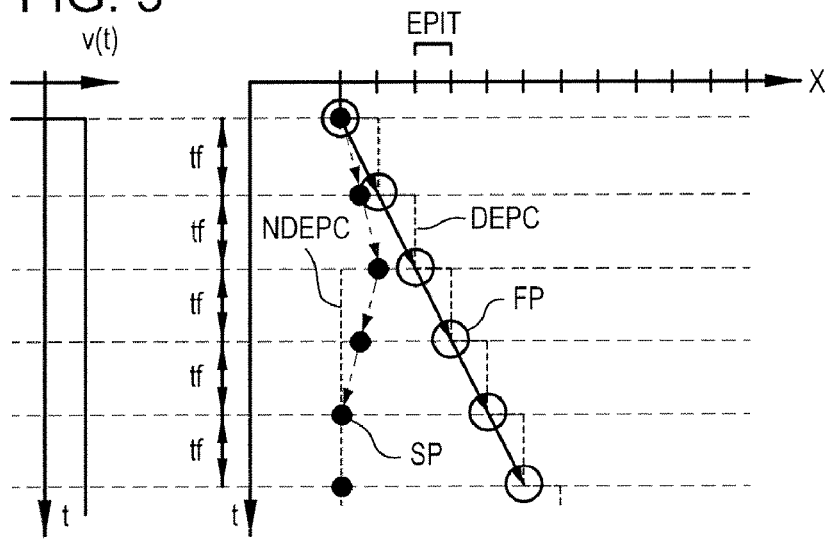
FIG. 3 shows the principle of separation by means of a field that travels at constant speed.

FIG. 3 shows a first aspect of the method according to the invention that carries out the separation by means of a field that translates at constant speed. Initially all particles are attracted into the same position (DEPC) corresponding to the only point of equilibrium. The field is translated by a discrete distance equal to the step of repetition (EPIT) at an average speed $V_F$ defined as the ratio between the step of repetition (EPIT) and the time $t_f$ elapsed for the field to progress by a distance equal to EPIT, that is $V_F=EPIT/t_f$. Only the particles (FP) able to move at a speed equal to or greater than $V_F$ can follow the translation continuously. The slower particles (SP) cannot keep up and end-up lagging behind. As a result they remain further back to the point of attraction of the field, so much as to suffer its attraction less and less stopping more or less near to the point of departure. Alternatively, these slow particles can be collected from a new point of equilibrium to be created for example at the coordinate of departure NDEPC. Optionally, it is possible to repeat the separation with a lower speed of translation (greater $t_f$) to further segregate the particles re-collected at the point of departure in populations with different speed.

Figure 4:
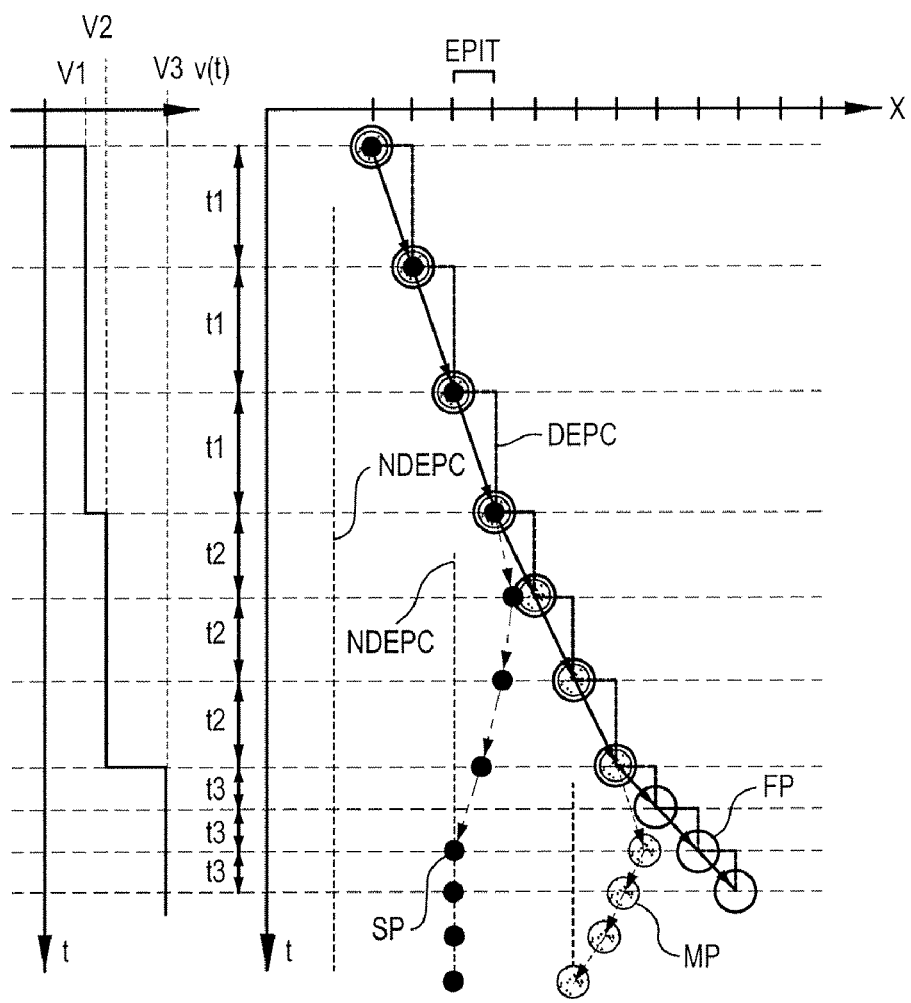
FIG. 4 shows the principle of separation by means of a field that travels at increasing speed.

Likewise to the above, separation can be done with the speed of translation of the point of attraction increased over time. In this case, illustrated for instance in FIG. 4, the particles initially follow the coordinate (DEPC) of the point of attraction, until the speed of translation exceeds their speed-limit in response to the field. In this case too it is possible to create new points of attraction (NDEPC) to collect the particles remained behind.

It is clear that the method also applies when the starting force field does not have a single point of equilibrium but a multiplicity of points.

The same technique of separation is practicable using continuous or discontinuous or piece-wise movements of the field of forces in space.

Method of Separation With Periodic Speed

The speed of translation of the force field (F) may also be periodic. This is especially useful when the force field has spatial periodicity (CPIT). For simplicity we define the number pitch=CPIT/EPIT representing the period of repetition of the field expressed in the number of electrodes. Some aspects of the method are listed hereunder.

Translation of Fast Particles

Figure 5:
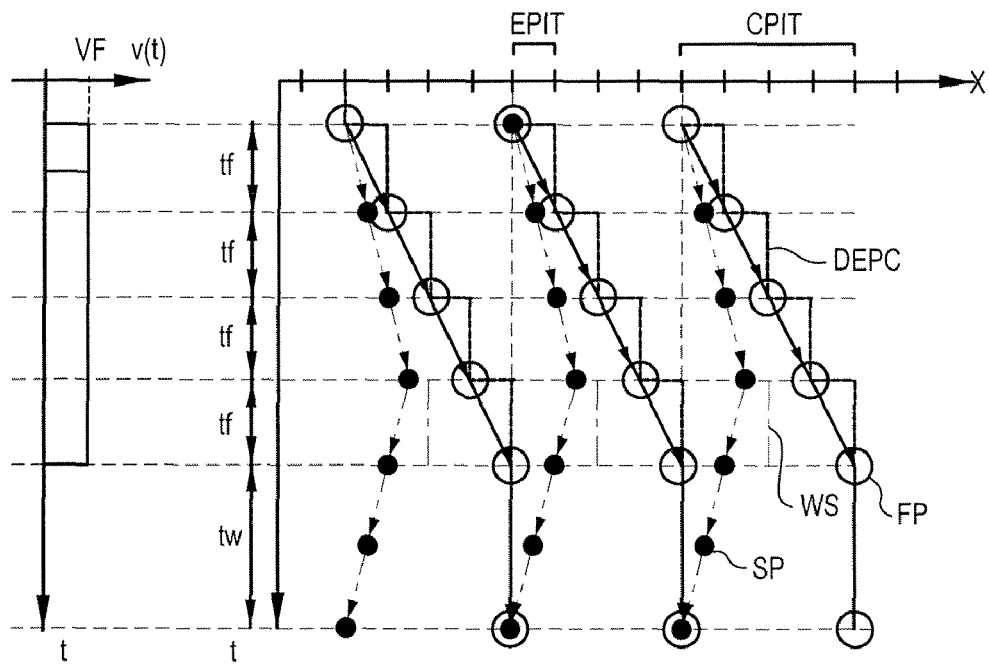
FIG. 5 shows the separation of the fastest particles by periodic translation of a periodic field.

FIG. 5 shows the separation of the fastest particles by translation with periodic speed (VF) having a period (tp) of a periodic force field. For a first time period pitch·$t_f$ the field translates at a constant average speed $V_F=EPIT/t_f$ such as to cause translation of the field equal to one spatial period (CPIT). For a second time period (tw) the field remains stationary, allowing the particles to reach a new point of equilibrium, corresponding to the original starting coordinate for the slower particles (SP) and to a new position, translated of the same extent as the translation of the field (CPIT), for the fastest particles (FP). In this case the critical speed that is distinguished, is:

$$v_{ws} = \frac{CPIT/2}{(\text{pitch}-1)\cdot t_f} = \frac{CPIT}{CPIT-EPIT}\cdot V_F/2.$$

In terms of time, a conventional critical time can be defined $$t_{ws} = \frac{EPIT}{v_{ws}} = 2\frac{CPIT-EPIT}{CPIT}t_f.$$

The particles that take longer than this time to complete a step will return to the position of departure. In reality, the force along the X axis is normally not constant. Therefore also the limiting speed that is obtained when there is equilibrium with the viscous friction is not constant between WS and DEPC. Accordingly, the above formula is indicative and it must be empirically corrected or determined by means of numerical simulations to have a more precise value. The waiting time (tw), in which the field remains stationary to allow settling, in the original position for the slower particles (SP), in the new position for the fastest particles (FP), is indicatively equal to at least $t_w=\alpha_w(\text{pitch}-2)\cdot t_f$, where the factor $\alpha_w \geq 1$ takes account of the fact that the speed of settling is typically lower than that during translation. Indeed, during translation the particles are for most of the time in regions of the field where the force is more intense, and they are therefore moving faster.

The total period is therefore $t_p=[\text{pitch}+\alpha_F\cdot(\text{pitch}-2)]\cdot t_f$. We are able from this to define the average speed of separation $v_{sep}=CPIT/t_p=V_F/[\text{pitch}+\alpha_F\cdot(\text{pitch}-2)]$, at which the fast particles (FP) move in the period, that is those for which $v \geq v_{ws}$.

Figure 6:
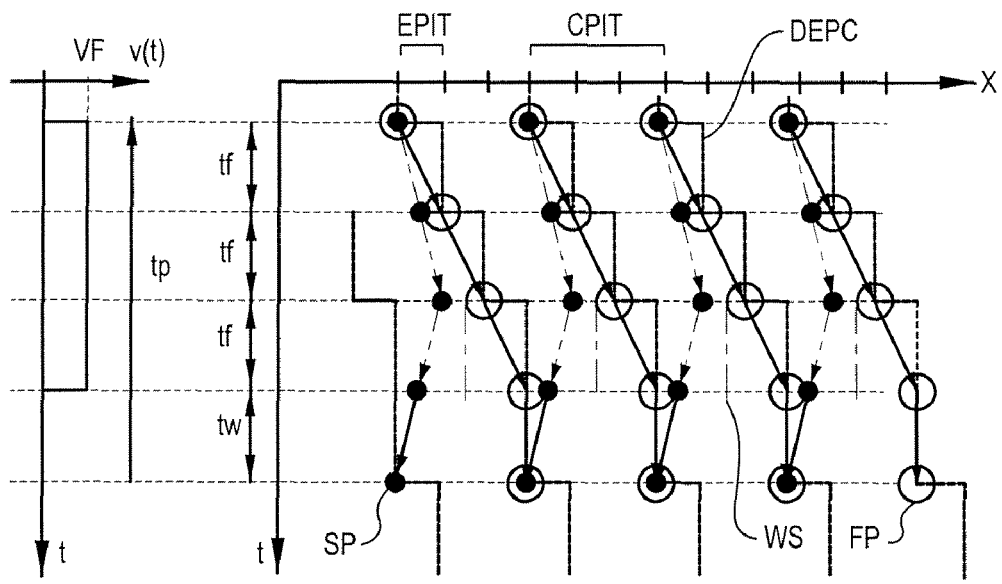
FIG. 6 shows the separation of the fastest particles by periodic translation of a periodic field for a different field configuration.

FIG. 6 shows the separation of the fastest particles as described above for a different field configuration.

Translation of Slow Particles

Figure 7:
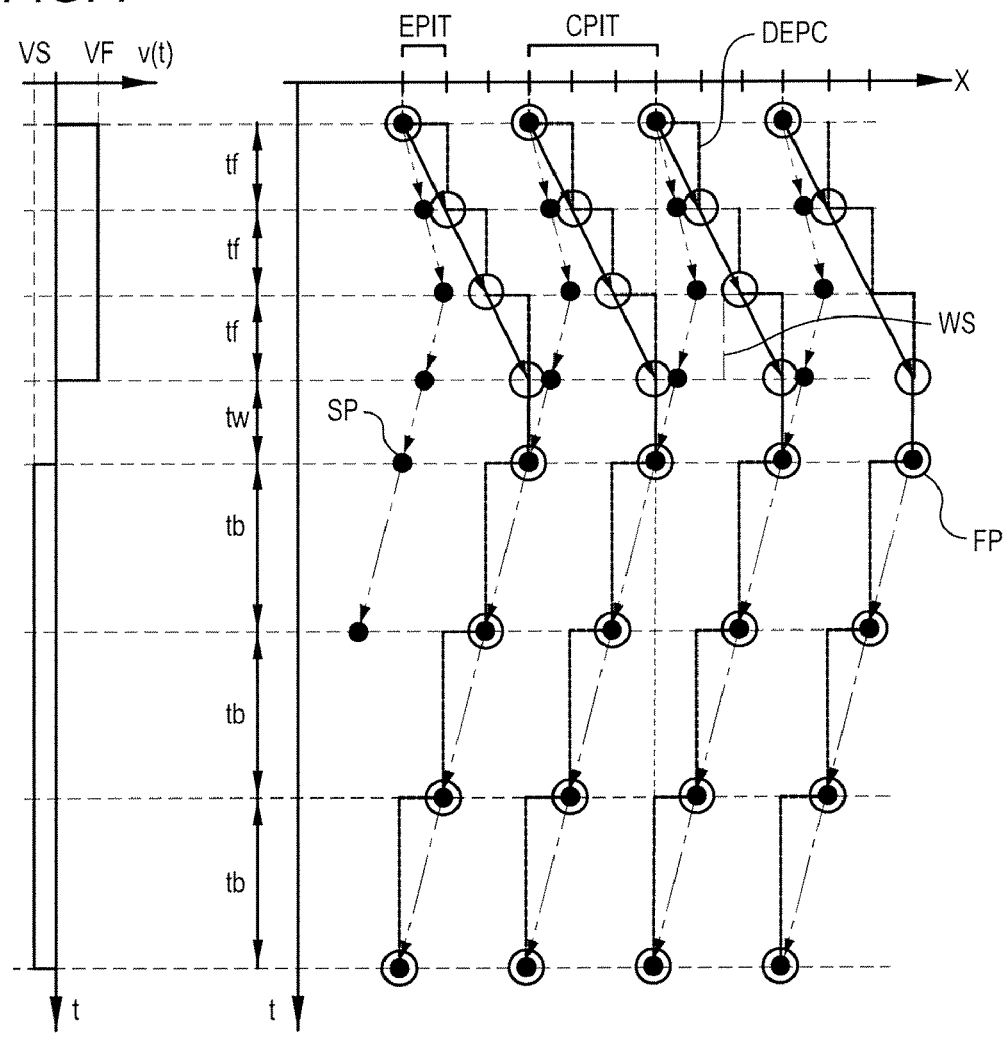
FIG. 7 shows the separation of the slowest particles by periodic translation of a periodic field.

FIG. 7 shows the separation of the slower particles by translation with speed (VF) periodic (tp) in a periodic force field. The method is, for a first part, entirely similar to the preceding method of separation of fast particles in a first direction, to which a second part is added during which both the fast particles (FP) and the slow ones (SP) are translated in a second direction, opposite to the first one, so as to obtain a net translation of the slower particles (SP) in the second direction and no movement of the fastest particles. The critical speed $v_{ws}$ and critical time $t_{ws}$, remain those defined for the preceding case, even if in this case the particles that are translated are those with lower speeds, $v \leq v_{ws}$, and longer time to complete a step, $t > t_{ws}$. The time $t_b$ defines a second speed limit. The particles that are too slow (for which $v < v_{ws2} = \text{EPIT}/t_b$) are not able to entirely follow the movements in the second direction. Therefore they lose the synchronism with the movements of the field and remain substantially stationary or they barely move in a direction that is difficult to predict. The total period of the cycle is $t_p = \text{pitch} \cdot (t_f + t_b) + t_w$. From this, one obtains the average speed of separation $v_{sep} = \text{CPIT}/t_p = \text{CPIT}/[\text{pitch} \cdot (t_f + t_b) + t_w]$, at which the selected particles (SP) move in the period, that is those for which $v < v_{ws}$.

Translation of Slow and Fast Particles in Opposite Directions

Figure 8:
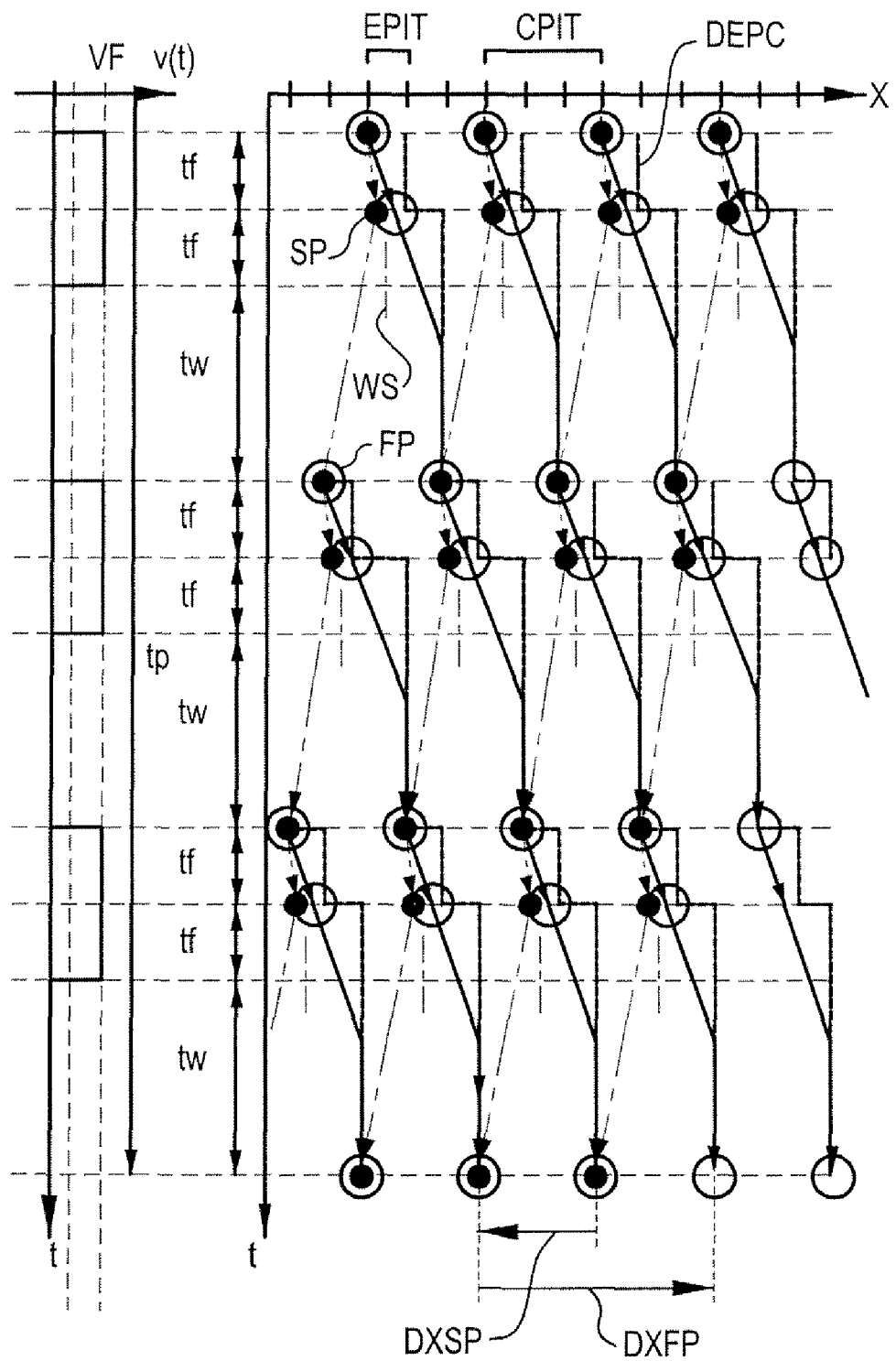
FIG. 8 shows the separation in opposite directions of the fastest particles and of the slowest particles by periodic translation of a periodic field.

FIG. 8 shows the separation in opposite directions of the fastest particles and of the slowest particles by periodic translation in a periodic field.

For a first time period $(\text{pitch}-1) \cdot t_f$ the field translates in a first direction at a constant average-speed in the spatial period EPIT equal to $V_F = \text{EPIT}/t_f$ such as to cause total translation of the field equal to $(\text{pitch}-1) \cdot \text{EPIT}$. For a second time period (tw) the field remains immobile, allowing the particles to reach a new point of equilibrium, varying its coordinate, with reference to the original position and the direction of translation of the field, of $-\text{EPIT}$ for the slower particles (SP) and CPIT$-$EPIT for the fastest particles (FP), In this case the critical speed that is distinguished is:

$$v_{ws} = \frac{\text{CPIT} - 2 \cdot \text{EPIT}}{2} \cdot \frac{1}{(\text{pitch}-2) \cdot t_f} \cdot V_F/2.$$

And the conventional critical time is $t_{ws} = \text{EPIT}/v_{ws} = 2 \cdot t_f$. The particles that take longer than this time to complete a step will return to the category of slow particles (SP), the ones that take less to the category of fast particles (FP).

The second time period in which the field remains immobile to allow the slow particles to reach the new point of equilibrium must be greater than $t_w = \alpha_w (\text{pitch}-1) \cdot t_f$, where the factor $\alpha_w \geq 1$ takes account of the fact that the settling-time to reach the new point of equilibrium starting from the coordinate WS is typically greater than the time required from a point of equilibrium to WS, as discussed above. In this case, too, the real value of $t_w$ determines a further limit. Particles that are excessively slow that are not able in this time to recover the point of equilibrium at $-\text{EPIT}$ lose their synchronism.

Since the above described translation should be made a number of times equal to pitch to complete a translation equal to the period of the field, the period of the cycle of separation can be defined as $$t_p = \text{pitch} \cdot [(\text{pitch}-1) \cdot t_f + t_w] = \text{pitch} \cdot [(1 + \alpha_w)(\text{pitch}-1) \cdot t_f]$$

In this period the slow particles translate by DXSP$=-$pitch$\cdot$EPIT and the fast ones by DXFP$=$pitch$\cdot$(pitch$-$1)$\cdot$EPIT. The speed of separation is $$v_{sepFP} = \frac{\text{EPIT}}{(1 + \alpha_w) \cdot t_f}$$

and for the fast particles (FP) and $$v_{sepSP} = -\frac{\text{EPIT}}{(1 + \alpha_w) \cdot (\text{pitch}-1) \cdot t_f}$$

for the slow particles (SP).

Figure 9:
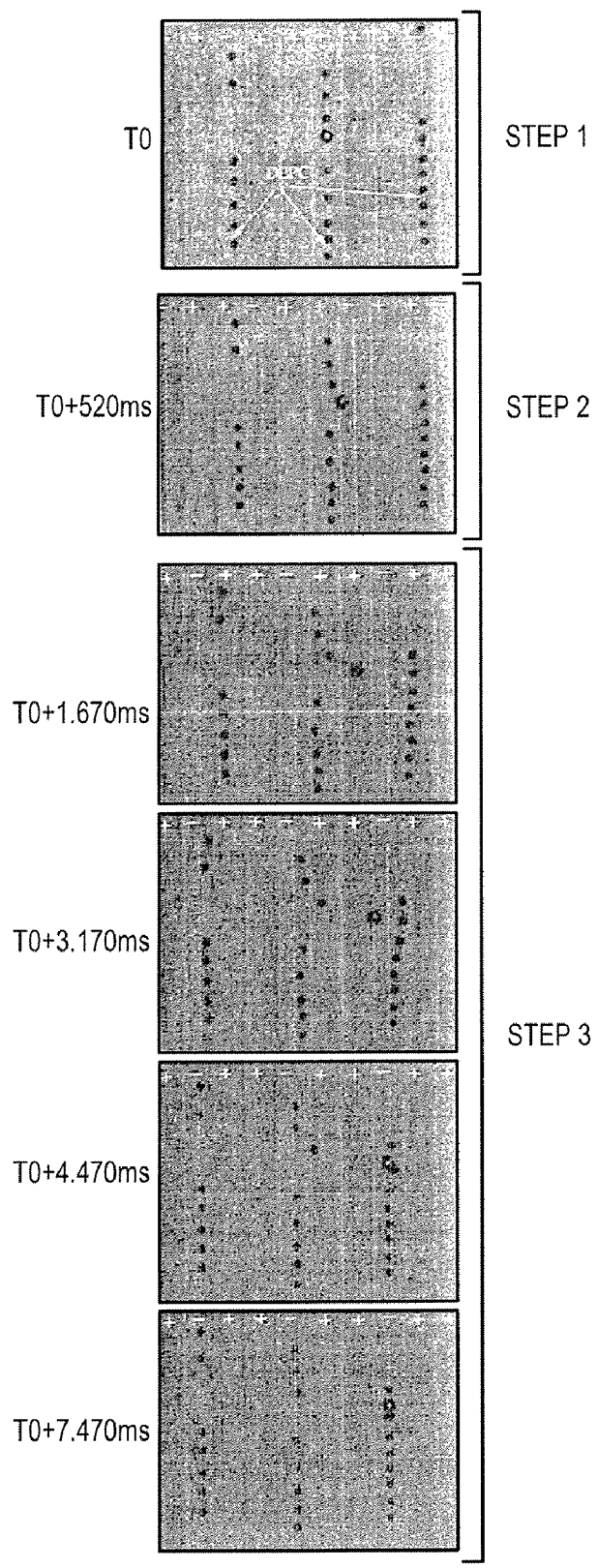
FIG. 9 shows the experimental results of separation in opposite directions.

FIG. 9 shows experimental results of separation in opposite directions with microbeads of polystyrene of 10 μm (SP) and 25 μm (FP) in an aqueous solution, trapped by NDEP in mobile cages of dielectrophoresis, on a device with elongated electrodes 45 μm wide and a gap of 5 μm (EPIT=50 μm). The conductive transparent cover makes a micro-chamber of 130 μm in height. The applied voltages are 4.7 Vpp at 1 MHz. In correspondence with the electrodes with phase (−), as the cover, the force cages (DEPC) are made (with pitch=3). The photos refer to the initial condition (STEP1) and to the following two steps (STEP2, STEP3) for the first iteration of translation of the field as per the diagram of FIG. 8.

It is evident to experts in the sector with ordinary capacities that other methods can be realized, according to the invention, as a combination of the above methods. For instance the periodic translation of fast particles in which, in the period, the field translates by a multiple of the spatial period of the field. Or the repetition in sequence of the separation with periodic speed of fast particles, but for speed ($V_F$) of the force field decreasing, so as to segregate the particles of the initial population in a series of groups, where each group is characterized by a speed interval.

It is moreover evident that it is also easy to generalize, as concerns the case of NDEP, the above described methods to cases in which the dimensions of the cage are multiples of a single electrode (e.g. the cage is generated by two adjacent electrodes in phase (−) with the cover, and surrounded by electrodes in the opposite phase (+), instead of by a single electrode).

It is lastly evident that the above described case relating to a translation of the force field (F) can easily be generalized to other types of movement, such as for instance a rotation, as could be useful for symmetrical array of electrodes in relation to a point (instead of an axis). For simplicity nevertheless reference will be made, also in the continuation of the description, to translations.

Method of Separation with Non-Uniform Voltages

Figure 10:
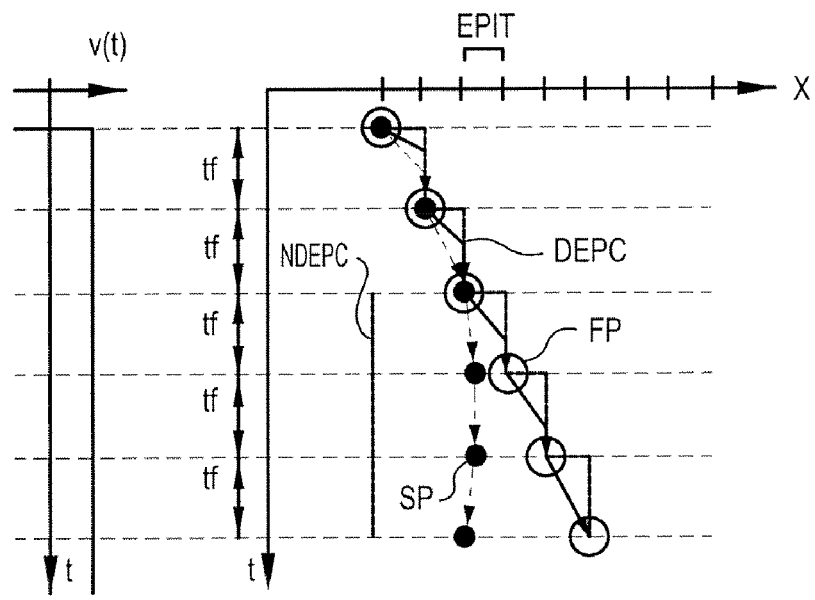
FIG. 10 shows the separation by means of translating fields of decreasing intensity.

In addition, it is possible to vary the intensity of the voltages applied to the electrodes during the translation. This generally involves a variation in the intensity of the field, that nevertheless maintains the same configuration for the force lines. For instance, it is possible to translate the field (F) at a constant speed to separate the fast particles, but to decrease its intensity during the time, so that only the more responsive particles (FP) follow the field, while those (SP) less affected by the field, in relation to the force of viscous friction, remain behind and lose their step. One example is given in FIG. 10.

Method of Separation with Non-Uniform Array of Electrodes

In the above examples we have considered a regular array of electrodes, of equal width, with spatial periodicity EPIT. Another aspect of the method according to the invention covers the case in which the array of electrodes is irregular. For example, it is possible to use electrodes of fixed dimensions but with a variable distance between the electrodes, or electrodes of varying dimensions with the same distance between the electrodes or variable dimensions both in their width and for the distance between the electrodes.

In these cases, besides varying the position of the points of equilibrium of the force field, its intensity varies during the translation, and in general the shape of the field also varies, that is the lines of force are not only translated but distorted too.

Likewise to the descriptions for the preceding methods it is possible to separate the particles that substantially follow the translation of the field from those that are not able to keep step, or, by exploiting the non-homogeneity of the field, particles of different diameter can be separated by pushing them both toward the same direction until the field deforms so much as to no longer be able to transport just one of the two types of particles. It is moreover evident that the same method of separation can be applied to the generic case of the separation of more than two types of particles.

Method of Separation with Only Two Field Configurations

Figure 14:
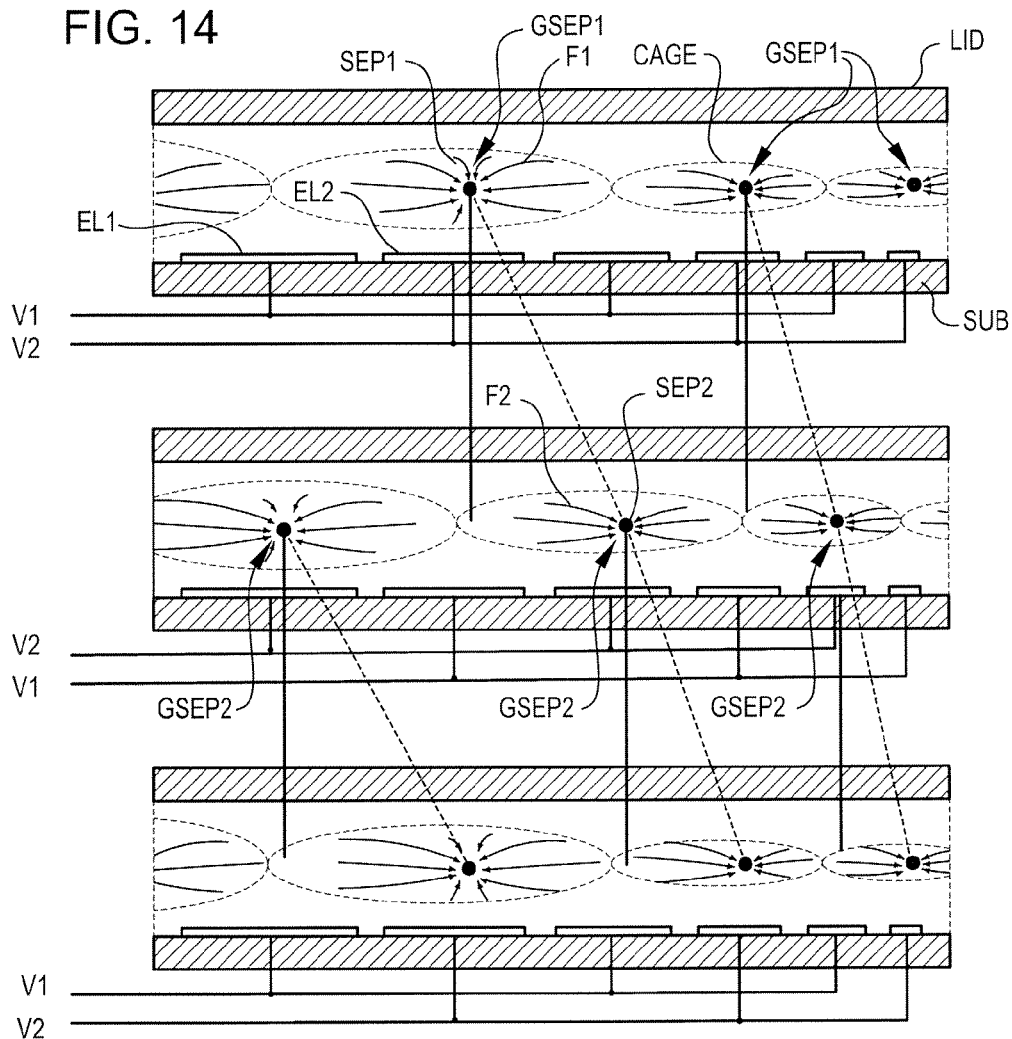
FIG. 14 shows the principle of separation by means of only two groups of stable equilibrium points.

In the above examples we have considered a succession of configurations of forces in the space; the minimum number of configurations of forces, necessary to permit the movement of particles in a specific direction and therefore their separation, is two. Indeed, as shown in FIG. 14, it is possible with an appropriate distribution of electrodes and applied voltages (V1,V2) to make just two distributions of forces (F1, F2) characterized by groups of points of stable equilibrium (GSEP1, GSEP2) such that any first point of equilibrium (SEP1, SEP2) of one of said groups (GSEP1, GSEP2) is unequivocally included inside the basin of attraction of a single second point of stable equilibrium (SEP2, SEP1) of the other group (GSEP2, GSEP1), and that said second point in its turn is not contained in the basin of attraction of said first point (SEP1, SEP2); in this way passing from one configuration of forces to the following one, the particles are moved in a specific direction; returning to the previous configuration of forces, however, the particles do not reverse the motion but continue in the same direction. By alternating the two configurations of forces at an appropriate speed, it is possible to move the more responsive particles (FP) leaving the less responsive ones (SP) stationary or behind. This method requires both a spatial non-homogeneity and a spatial non-repeatability of the field; this can be obtained, for example, by means of the apparatus subject of the invention as described in detail hereunder.

According to this method it is possible to separate particles of at least two types (FP, SP), so as to obtain a net movement of only said particles of a first type (FP) by changing the configuration of the field of forces at a frequency substantially comparable to the inverse of the settling-time of the particles of a first type (FP) at the new point of equilibrium, but greater than the inverse of the settling-time of the particles of at least a second type (SP).

According to this method it is also possible to separate particles of at least two sizes (BP, LP). In fact, when a particle (BP) is much bigger than the basin of attraction of a stable equilibrium point, so that it is subject to the attraction of more than one point of equilibrium, the particle does not move, since the resultant of forces is not enough to propel the particle (BP) toward either of the equilibrium points. Hence, to carry out the separation of small particles (LP) one can generate a first distribution in the space of a force field (F1) characterized by a first set of points of stable equilibrium (GSEP1) for said particles (BP, LP); and at least a second distribution in the space of a force field (F2) characterized by a second set of points of stable equilibrium (GSEP2) for said particles (BP, LP); wherein said two distributions of forces (F1, F2) are such that any first point of equilibrium (SEP1, SEP2) of one of said groups (GSEP1, GSEP2) is unequivocally included inside the basin of attraction of a single second point of stable equilibrium (SEP2, SEP1) of the other group (GSEP2, GSEP1), and that said second point in its turn is not contained in the basin of attraction of said first point (SEP1, SEP2); and that the size of the basin of attraction of each first point (SEP1, SEP2) is greater or less than the size of the basin of attraction of said single second point of stable equilibrium (SEP2, SEP1) containing it; and then can alternate the distributions (F1, F2) of said force field at a frequency comparable to the inverse of the settling-time of both types of particles (BP, LP), so as to move said particles (BP, LP) from one new point of equilibrium to the next one until the size of the particles is compatible with that of the basin of attraction. If the size of the basins of attraction gradually reduces, the big particles (BP) will in fact stop moving earlier than the small particles (LP), so as to obtain a net overall movement of the small particles (LP) greater than the net overall movement of the large particles (BP).

Figure 11:
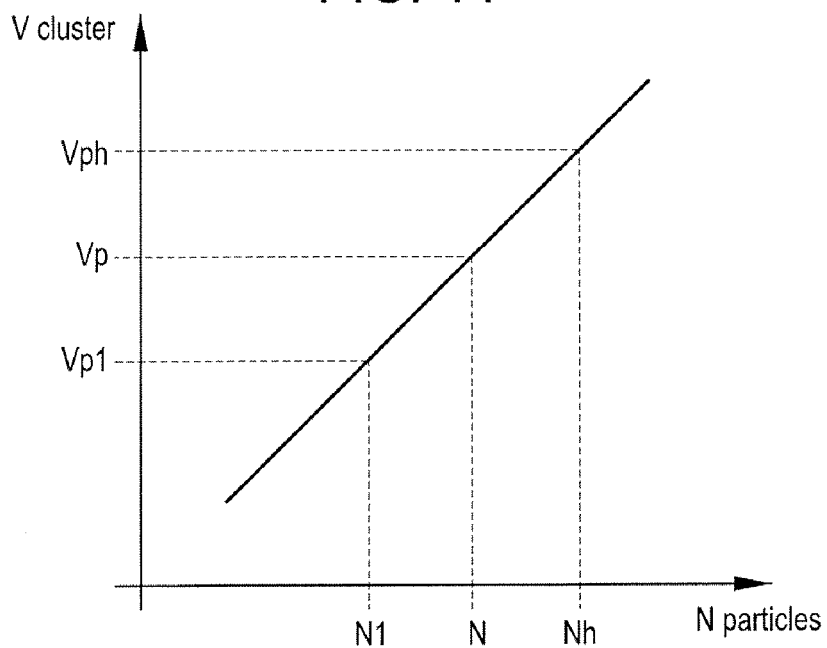
FIG. 11 shows a diagram of the relationship between the speed of a group of particles and the number of particles composing it.

Method of Quantifying Groups of Particles by Indirect Measurement of the Translation Speed In the above methods it is an advantage that the density of the particles subject to the field is not such as to substantially affect the speed of translation of the single particles because of their mutual interactions. In fact, when grouped together, even small particles behave as larger particles, approximately with a volume equivalent to the sum of the volumes of the single particles, as shown in FIG. 11.

Figure 13:
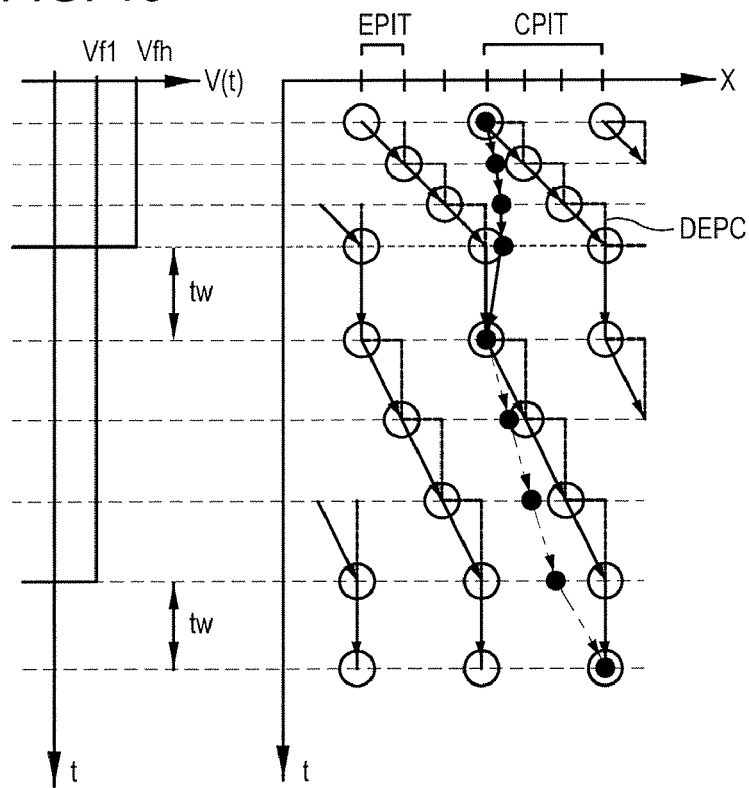
FIG. 13 shows the principle of determination of the critical speed of a group (or single) particles, to determine its number (or diameter).

According to a further method of the invention, illustrated in FIG. 13, this effect is utilized to identify the quantity of particles (N) that form the sample to analyze.

Starting from a homogeneous sample with an unknown concentration of particles of known speed, the position of a group of particles is determined.

Then the point of stable equilibrium between two positions is moved, at known speed (Vfh), verifying whether the group responds to this change in the field with a corresponding movement of the rest position. If this is not so, the critical speed of the group of particles is evidently lower than the speed of movement of the point of stable equilibrium (Vfh). After a waiting period (tw), to allow the particles to settle at their initial point, the movement of the field is repeated at a lower speed (Vfl), until the particles are able to follow the movement of the rest position, which indicates that the critical speed of the particles is higher. Repeating the measurement so as to identify at least one speed of movement of the field greater than the critical speed and one lower, an interval is determined inside which the critical speed of the group of particles must necessarily be included, which corresponds to a specific range of quantity of particles. In this way, knowing the range in which the critical speed $v_{ws}$ falls we can calculate the total volume of the particles in the group (with a certain approximation related to the width of the range) by using the ratio between volume and speed that is ideally linear. If this ratio is not linear, the ratio can be determined experimentally, producing a pre-characterization of the parameter subject of the measurement, that is the quantity of particles in the sample. The search for the critical speed can be made in various ways, for example with binary or linear searching.

The position can be measured with integrated or external sensors of the optical type, impedentiometric, etc., in accordance with the known art.

If the sensitivity of these sensors were not suitable to detect the presence of the initial quantity of the particles on an electrode, according to the invention the quantity should be increased, concentrating the content of several cages, to allow detection and exploiting the linear relationship or the pre-characterization to determine the measured quantity.

Figure 12:
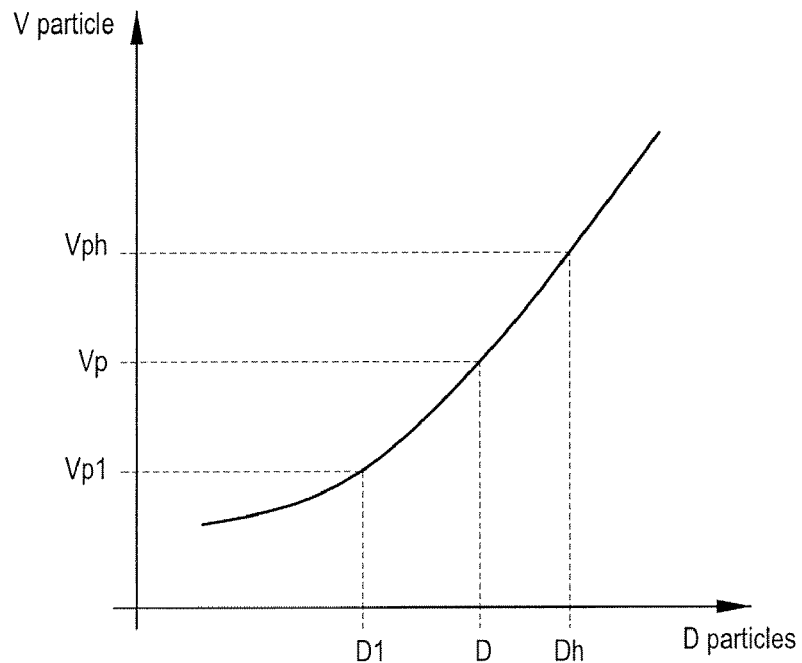
FIG. 12 shows a diagram of the relationship between the speed of particles made of the same homogeneous material and the diameter of the particle.

Method of Determining the Size of Particles by Indirect Measurement of the Translation Speed The above-described method for the quantification of particles can be applied in a similar manner to the problem of determining the size of particles. For this purpose, we act on groups of non-interactive particles or ones with negligible interaction between each other. In this case, as illustrated in FIG. 12, to obtain the size of the single particles we use the relationship between the speed of the particles (Vparticle) and their diameter (Dparticle).

Apparatus for the Separation of Particles

Figure 15:
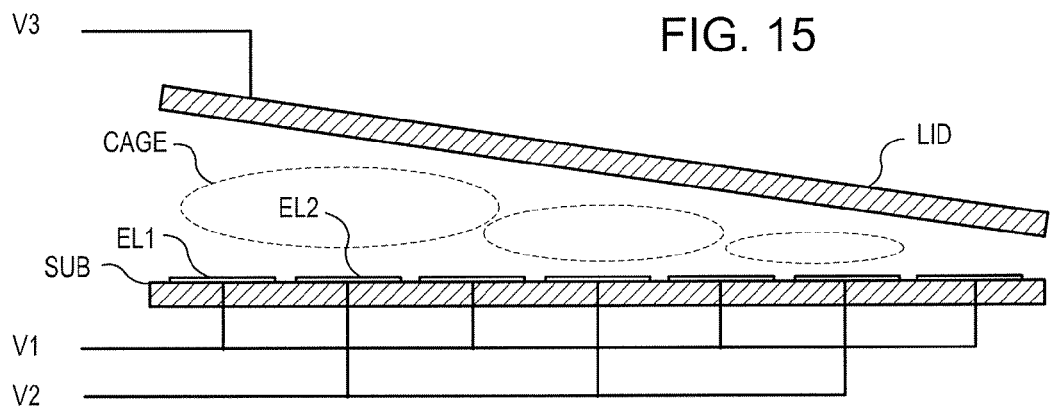
FIG. 15 shows a device to bring about the method of separation by means of only two groups of points of stable equilibrium.

The subject of this invention is also an apparatus to make appropriate field configurations that are necessary for the selective movement of particles; this device, in one of its typical implementations, has two array of electrodes (EL1, EL2) and, if necessary, a cover (LID); means to apply an electric potential (V1) to said first array of electrodes (EL1) and at least a second potential (V2) to said at least a second array of electrodes (EL2) are also included even if not shown because substantially of know kind; said electrodes and said means to apply an electric potential to said electrodes are operatively associated such that on the electrodes (EL1, EL2) appropriate stimuli (V1, V2) are applied to make at least two different spatial distributions of forces (F1, F2), each characterized by a group of points of stable equilibrium (SEP1, SEP2). A characteristic of these points of stable equilibrium is that each one is unequivocally included in just one of the basins of attraction of the stable-equilibrium points of the other configuration of forces. In this way the device subject of the invention permits trapping particles and moving them in a direction at a speed that depends on the speed with which the two configurations of forces are alternated and on the responsiveness of the particles. These distributions of forces can be made, for example, by utilizing electrodes of increasing or decreasing width and constant inter-electrode distance (FIG. 14) or with an increasing or decreasing inter-electrode distance and constant width. Another implementation can be based on the use of electrodes of constant dimensions and constant inter-electrode distance but with an increasing or decreasing distance between the electrodes and the cover (FIG. 15). A combination of the above-described implementations is obviously possible.

What is claimed:

1. A method to separate a sample of particles comprising at least first and second particles, comprising:
   i. generating a first distribution in the space of a first force field characterized by a first set of points of stable equilibrium for the first and second particles;
   ii. generating at least a second distribution in the space of a second force field characterized by a second set of points of stable equilibrium for the first and second particles, wherein the first and second distributions of forces are such that:
      a) a first point of stable equilibrium of one of the first and second sets of points of stable equilibrium is included inside a basin of attraction of a single second point of stable equilibrium of the other one of the first and second sets of points of stable equilibrium, and
      b) said second point of stable equilibrium is not contained in a basin of attraction of said first point of stable equilibrium; and
   iii. alternating between the first and second distributions at a frequency substantially comparable to the inverse of the settling-time of the first particles at a new point of stable equilibrium, but greater than the inverse of the settling-time of the second particles to obtain a net movement of only the first particles.

2. A method to separate a sample of particles comprising at least first and second particles, the first particles being larger than the second particles, comprising:
   i. generating a first distribution in the space of a force field characterized by a first set of points of stable equilibrium for said first and second particles;
   ii. generating at least a second distribution in the space of a force field characterized by a second set of points of stable equilibrium for said first and second particles, wherein said first and second distributions are such that:
      a) a first point of stable equilibrium of one of the first and second sets of points of stable equilibrium is included inside a basin of attraction of a single second point of stable equilibrium of the other one of the first and second sets of points of stable equilibrium,
      b) said second point of stable equilibrium is not contained in a basin of attraction of said first point of stable equilibrium, and
      c) the size of the basin of attraction of the first point of stable equilibrium is greater or less than the size of the basin of attraction of said single second point of stable equilibrium containing it; and
   iii. alternating between the first and second distributions at a frequency comparable to the inverse of the settling-time of the first and second particles, so as to move the first and second particles from one point of equilibrium to a next point of equilibrium until the size of the particles is compatible with that of the basin of attraction so as to obtain a net overall movement of the second particles greater than a net overall movement of the first particles.

3. The method as in claim 1, wherein said first and second sets of points of stable equilibrium are generated by at least one set of electrodes of increasing or decreasing width distributed with a constant step of spatial repetition.

4. The method as in claim 1, wherein said first and second sets of points of stable equilibrium are generated by at least one set of electrodes of constant width distributed with a non-constant step of spatial repetition.

5. The method as in claim 1, wherein said first and second sets of points of stable equilibrium are generated by at least one set of electrodes of increasing or decreasing width distributed with a non-constant step of spatial repetition.

6. The method as in claim 1, wherein said first and second sets of points of stable equilibrium are generated by at least one set of electrodes of constant dimensions distributed with a constant step of spatial repetition, supplied with voltages of non-constant amplitude.

7. The method as in claim 2, wherein said first and second sets of points of stable equilibrium are generated by an array of electrodes and by at least one cover electrode facing said array of electrodes and angled with respect thereto so as to have an increasing or decreasing distance between the electrodes and the cover electrode.

* * * * *